(12) United States Patent
Miener et al.

(10) Patent No.: US 7,843,641 B2
(45) Date of Patent: Nov. 30, 2010

(54) ILLUMINATED OPTICAL INSPECTION PRISM APPARATUS

(75) Inventors: Steven John Miener, Florissant, MO (US); Kevin Lee Brown, Saint Peters, MO (US)

(73) Assignee: The Boeing Company, Chicago, IL (US)

( * ) Notice: Subject to any disclaimer, the term of this patent is extended or adjusted under 35 U.S.C. 154(b) by 582 days.

(21) Appl. No.: 11/851,172

(22) Filed: Sep. 6, 2007

(65) Prior Publication Data

US 2010/0271811 A1  Oct. 28, 2010

(51) Int. Cl.
  *G02B 27/14* (2006.01)
  *G03B 21/26* (2006.01)
  *H04N 7/00* (2006.01)
(52) U.S. Cl. .......................... 359/629; 353/28; 348/115
(58) Field of Classification Search ......... 359/629–639,
    359/13–14, 404, 407, 409–410, 618–619,
    359/625; 345/7–9; 631/633, 640; 351/41–176;
    348/115; 349/11; 353/11–12, 28, 119; 340/438,
    340/980, 995.1, 815.47, 815.74
  See application file for complete search history.

(56) References Cited

U.S. PATENT DOCUMENTS 5,212,471 A * 5/1993 McDonald .................... 345/7

6,474,809 B2 * 11/2002 Tanijiri et al. ................. 351/41
6,751,379 B2 * 6/2004 Capewell et al. .............. 385/36

FOREIGN PATENT DOCUMENTS

| DE | 19720330 C1 | 11/1998 |
| DE | 10161914 C1 | 9/2003 |
| EP | 1256945 A2 | 11/2002 |
| GB | 361650 A | 11/1931 |
| WO | 2005064321 A | 7/2005 |

* cited by examiner

*Primary Examiner*—Scott J Sugarman
*Assistant Examiner*—Dawayne A Pinkney
(74) *Attorney, Agent, or Firm*—Yee & Associates, P.C.; Dennis R. Plank (57) ABSTRACT

A method and apparatus for inspecting transparent materials. An optical inspection apparatus comprises a prism, a mirror, and a light source. The prism has a first end, a first side, and a second side. The first side is opposite the second side, the first end is located between the first side and the second side, the first end has an angled surface, and the prism is capable of bending light. The first side is around parallel to the second side. The mirror is on the angled surface. The mirror is capable of redirecting light entering the prism on the first side along a directed line of sight to the second side along a line of sight to a viewer. The light source is attached to another surface on the first end. The light source is capable of transmitting light through the prism along the directed line of sight.

18 Claims, 7 Drawing Sheets

ILLUMINATED OPTICAL INSPECTION PRISM APPARATUS

This invention was made with Government support. The government has certain rights in this invention.

BACKGROUND INFORMATION

1. Field

The present disclosure relates generally to inspecting materials and in particular to a method and apparatus for inspecting transparent materials. Still more particularly, the present disclosure relates to a method and apparatus for inspecting a transparent material attached to a frame or other component.

2. Background

An aircraft canopy is a transparent enclosure for the cockpit that may be used on some types of aircraft. The function of a canopy is to provide a weather proof and reasonably quiet environment for the occupant or occupants of the aircraft. A canopy is typically aerodynamically shaped to minimize drag on an aircraft. A canopy includes a transparent material that is captured or attached to a frame. This transparent material may be, for example, glass or acrylic. The transparent material is also referred to as a transparency. The frame of the canopy is attached to the aircraft and allows the canopy to move, or open and close. The transparency typically is machined to include a row of holes around the periphery to attach the transparent material to a structural frame. This transparency is then attached to the frame with fasteners, such as bolts or other fastening system, being placed through the hole in the transparency and an attachment point in the frame. Hundreds of fasteners may be used to attach the transparency to the frame. Typically, a fastener may be found around every inch along the transparency.

In manufacturing canopies, and in maintenance, it is desirable to determine whether cracks have occurred and/or propagated from any of the holes in the transparent material. Inspections of these holes may be made visually, in some cases. In many cases, an unaided viewer may be unable to see the hole clearly enough to determine whether cracks have occurred or propagated. The hole, however, in many cases, is obscured by the frame or other components in the canopy.

In some cases, a simple prism with a faceted surface may be used to reflect light rays to allow the viewer to see under or into the canopy frame to determine whether cracks have occurred or propagated from any of the holes where the transparent material is attached to the frame. This type of inspection system works in many cases. In some cases, however, the transparent material is located or positioned in the frame deep enough such that it is impractical or difficult to see whether cracks may have occurred or propagated. One manner in which the holes in the transparent material may be inspected, in this situation, is to disassemble portions of the canopy to expose the holes where the fastener attaching the transparent material to the frame of the canopy is located. The transparency, in some canopies, are bonded into the frame. With other canopies, the transparency may be attached with both fasteners and bonding. As a result, disassembly may be unfeasible with these types of designs.

Therefore, it would be advantageous to have a method and apparatus that overcomes these problems.

SUMMARY

The different advantageous embodiments provide a method and apparatus for inspecting transparent materials. In one advantageous embodiment, an optical inspection apparatus comprises a prism, a mirror, and a light source. The prism has a first end, a first side, and a second side, wherein the first side is opposite the second side, the first end is located between the first side and the second side, the first end has an angled surface, and the prism is capable of bending light. The first side is around parallel to the second side. The mirror is located on the angled surface, wherein the mirror is capable of redirecting light entering the prism on the first side along a directed line of sight to the second side opposite to the first side along a line of sight to a viewer. The light source is attached to another surface on the first end of the prism. The light source is capable of transmitting light through the prism along an axis that is approximately coaxial to the directed line of sight.

In another advantageous embodiment, an apparatus comprises a prism and a mirror. The prism has a first side and a second side, wherein the first side is opposite the second side. The mirror is located on a first end, wherein the mirror is capable of reflecting light from a directed line of sight through the second side to a selected point to a line of sight through the first side.

In yet another advantageous embodiment, a method is present for inspecting a transparent object attached to a structure. A first side of a prism is placed onto a surface of the transparent object attached to the structure, wherein an attachment point is present between the transparent object and the structure below a surface of the structure. A light is transmitted through a first end of the prism along a directed line of sight to the attachment point between the transparent object and the structure below the surface of the structure. A response to the transmitted light is redirected from the directed line of sight to a line of sight through a second side of the prism that is opposite to the first side with a mirror. The response is observed to view the attachment point. A determination is made as to whether the attachment point meets a requirement.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives and advantages thereof, will best be understood by reference to the following detailed description of an advantageous embodiment of the present disclosure when read in conjunction with the accompanying drawings, wherein:

DETAILED DESCRIPTION

Figure 1:
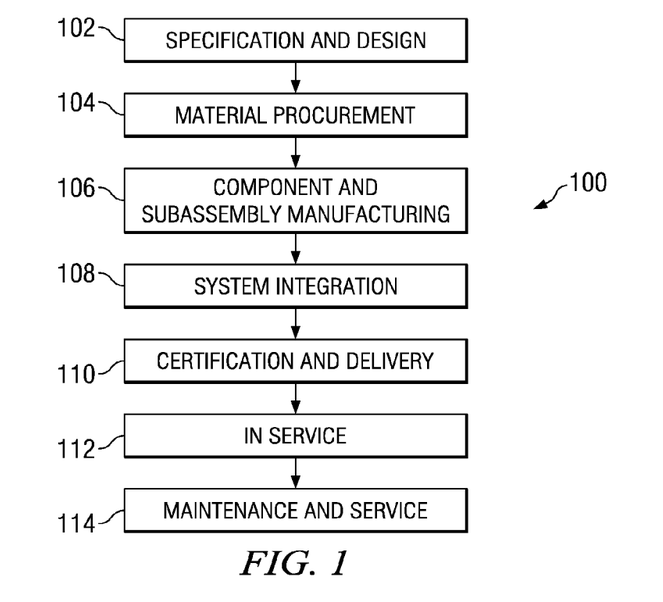
FIG. 1 is a diagram illustrating an aircraft manufacturing and service method in which an advantageous embodiment may be implemented.
Figure 2:
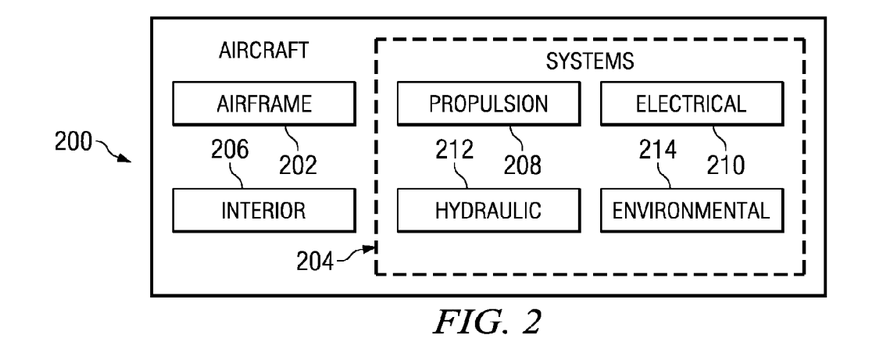
FIG. 2 is a diagram of an aircraft in accordance with an advantageous embodiment.

Referring more particularly to the drawings, embodiments of the disclosure may be described in the context of aircraft manufacturing and service method 100 as shown in FIG. 1 and aircraft 200 as shown in FIG. 2. Turning first to FIG. 1, a diagram illustrating an aircraft manufacturing and service method is depicted in accordance with an advantageous embodiment. During pre-production, exemplary aircraft manufacturing and service method 100 may include specification and design 102 of aircraft 200 in FIG. 2 and material procurement 104. During production, component and subassembly manufacturing 106 and system integration 108 of aircraft 200 in FIG. 2 takes place. Thereafter, aircraft 200 in FIG. 2 may go through certification and delivery 110 in order to be placed in service 112. While in service by a customer, aircraft 200 in FIG. 2 is scheduled for routine maintenance and service 114, which may include modification, reconfiguration, refurbishment, and other maintenance or service.

Each of the processes of aircraft manufacturing and service method 100 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of venders, subcontractors, and suppliers; and an operator may be an airline, leasing company, military entity, service organization, and so on.

With reference now to FIG. 2, a diagram of an aircraft is depicted in which an advantageous embodiment may be implemented. In this example, aircraft 200 is produced by aircraft manufacturing and service method 100 in FIG. 1 and may include airframe 202 with a plurality of systems 204 and interior 206. Examples of systems 204 include one or more of propulsion system 208, electrical system 210, hydraulic system 212, and environmental system 214. Any number of other systems may be included. Although an aerospace example is shown, different advantageous embodiments may be applied to other industries, such as the automotive industry.

Apparatus and methods embodied herein may be employed during any one or more of the stages of aircraft manufacturing and service method 100 in FIG. 1. For example, components or subassemblies produced in component and subassembly manufacturing 106 in FIG. 1 may be fabricated or manufactured in a manner similar to components or subassemblies produced while aircraft 200 is in service 112 in FIG. 1. Also, one or more apparatus embodiments, method embodiments, or a combination thereof may be utilized during production stages, such as component and subassembly manufacturing 106 and system integration 108 in FIG. 1, for example, by substantially expediting the assembly of or reducing the cost of aircraft 200. Similarly, one or more of apparatus embodiments, method embodiments, or a combination thereof may be utilized while aircraft 200 is in service 112 in FIG. 1, for example and without limitation, to maintenance and service 114 in FIG. 1. In these particular examples, the optical inspection apparatus, in the different advantageous embodiments, may be used during steps, such as component in subassembly manufacturing 106 and maintenance and service 114 in FIG. 1 to inspect transparent materials attached to other components. For example, the optical inspection apparatus, in the different advantageous embodiments, may be used to inspect the attachment of a canopy to a frame. Further, the different advantageous embodiments also may be applied to inspect the attachment of a window or portal in the passenger aircraft or cockpit of a commercial airliner.

The different advantageous embodiments recognize that the use of a simple prism to inspect the attachment of a transparent material to a frame is often insufficient. In view of this problem, the different advantageous embodiments provide a method and apparatus for optical inspection of a transparent material attached to a structure.

In one advantageous embodiment, an optical inspection apparatus comprises a prism, a mirror, and a light source. The prism has a first end, a first side, and a second side, wherein first side is opposite the second side, the first end is located between the first side and the second side, the first end has an angled surface, and the prism is capable of bending light. The first side is around parallel to the second side. Other depicted examples may illustrate a first side parallel to a second side, these sides do not need to be parallel and may be non-parallel in different advantageous embodiments. The mirror is located on the angled surface, wherein the mirror is capable of redirecting light entering the prism on the first side along a directed line of sight to the second side opposite to the first side along a line of sight to a viewer. The light source is attached to another surface on the first end of the prism. The light source is capable of transmitting light through the prism along an axis that is approximately coaxial to the directed line of sight.

Figure 3:
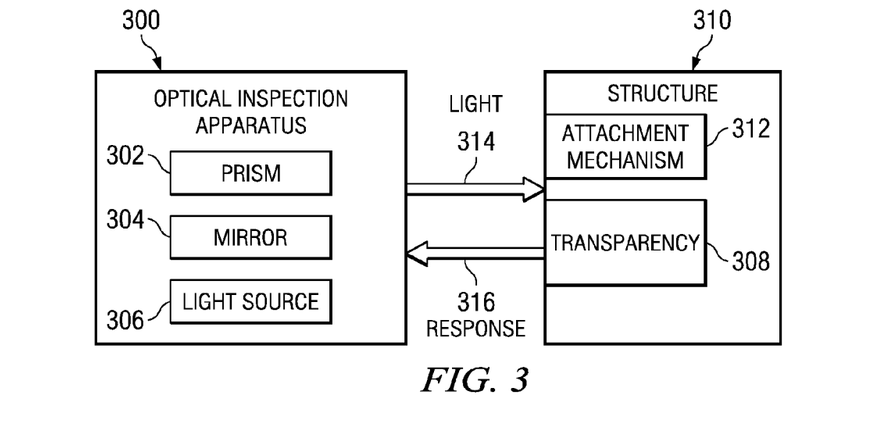
FIG. 3 is a block diagram illustrating an optical inspection apparatus used to inspect a transparency in accordance with an advantageous embodiment.

With reference next to FIG. 3, a block diagram illustrating an optical inspection apparatus used to inspect a transparency is depicted in accordance with an advantageous embodiment. In this example, optical inspection apparatus 300 includes prism 302, mirror 304, and light source 306.

Optical inspection apparatus 300 may be used to inspect transparency 308, which is attached to structure 310. Transparency 308 is a transparent material that may be used in or attached to structure 310. Transparency 308 may be, for example, a canopy, a window, or some other component. Structure 310 may be, for example, a frame of a canopy, a frame for a window, or some other structure in which a transparent material is placed and/or attached to structure 310.

In these examples, transparency 308 may be attached to structure 310 through a number of different mechanisms. For example, a fastening system may be placed through holes in transparency 308 into structure 310 to attach transparency 308 to structure 310. In other embodiments, transparency 308 may be bonded to structure 310.

Optical inspection apparatus 300 may be used to inspect the attachment of transparency 308 to structure 310 to determine whether maintenance is needed to maintain the attachment between these two components. In some cases, maintenance may be to replace the transparency with a new transparency. In other cases, the maintenance may be to rebond the transparency to the frame. In other cases, the maintenance inspection interval may be increased to monitor a discovered flaw in the transparency material or in a bonded joint. As a non-limiting example, optical inspection apparatus 300 may be used to inspect a hole through which attachment mechanism 312 is used to attach transparency 308 to structure 310. In this example, attachment mechanism 312 may be a fastener, such as a bolt and a nut. In other examples, attachment mechanism 312 may be a bonding agent that bonds transparency 308 to structure 310. When transparency 308 is bonded to structure 310, a mesh may be used as part of the bonding process, which may be visible for inspection to determine whether the bond is intact or deteriorating. In yet other advantageous embodiments, optical inspection apparatus 300 may be used to inspect a transparency in which attachment mechanism 312 includes both bonding and fasteners.

Light source 306 transmits light 314 into transparency 308 through prism 302. Response 316 is received in response to the transmission of light 314 into transparency 308. Response 316 is light that reflects and/or refracts from transparency 308 and/or other components within structure 310. Response 316 travels through prism 302 and is redirected by mirror 304 to a view point of an operator of optical inspection apparatus 300, in the different advantageous embodiments.

In these depicted examples, optical inspection apparatus 300 is preferably coupled to transparency 308 in a manner that allows light 314 to travel into transparency 308 with a minimum amount of refraction or reflection. In a similar manner, the coupling of optical inspection apparatus 300 to transparency 308 also reduces the reflection or refraction of light as response 316 returns to optical inspection apparatus 300.

Figure 4:
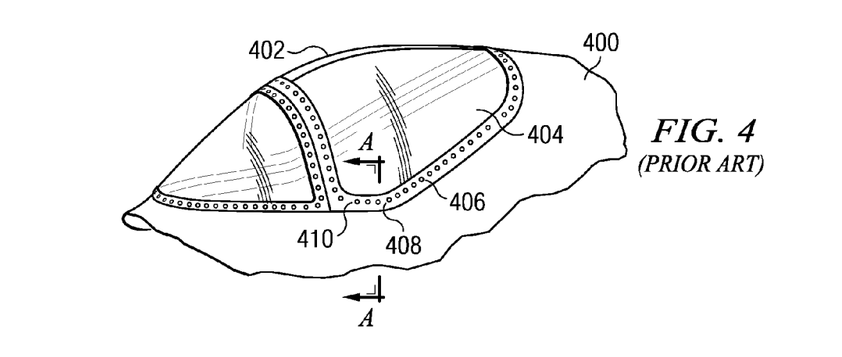
FIG. 4 is a view of an aircraft transparency installed in a frame with a plurality of fasteners in accordance with an advantageous embodiment.

Turning now to FIG. 4, a view of an aircraft transparency installed in a frame with a plurality of fasteners is depicted. In this example, a portion of aircraft 400 is depicted with canopy 402. Canopy 402 includes transparency 404 and structural frame 406. An optical inspection apparatus, such as optical inspection apparatus 300 in FIG. 3 may be used to inspect the attachment point of canopy 404 to structural frame 406. In this example, the attachment point may be a plurality of fasteners, such as fastener 408 and fastener 410.

Figure 5:
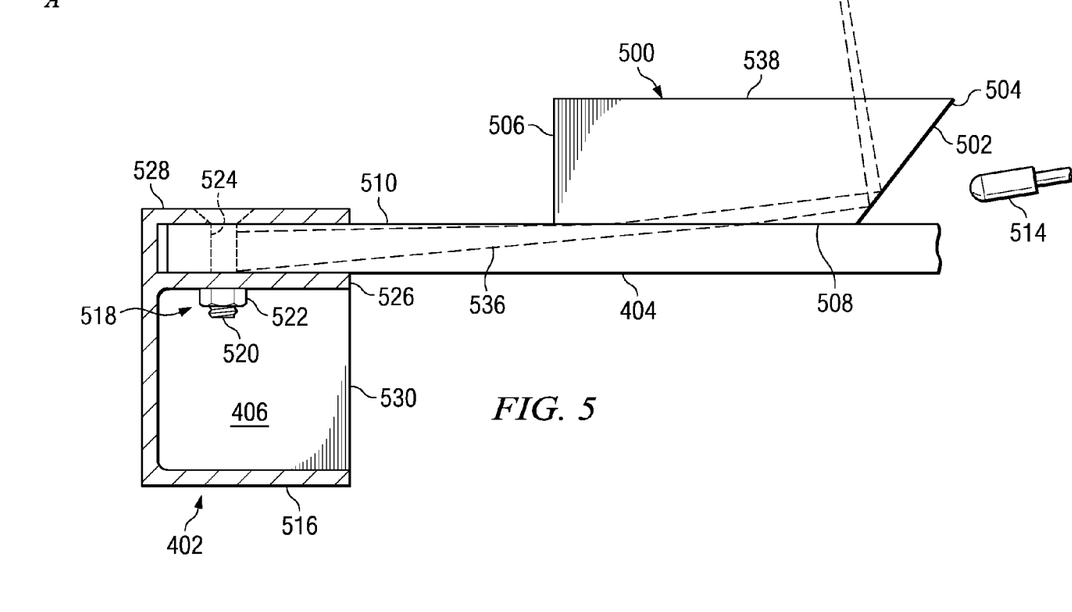
FIG. 5 is a diagram illustrating the operation of an optical inspection apparatus in accordance with an advantageous embodiment.

Turning now to FIG. 5, a diagram illustrating the operation of an optical inspection apparatus is depicted in accordance with an advantageous embodiment. In this example, prism 500 is an example of prism 302 within optical inspection apparatus 300 in FIG. 3. Prism 500 has mirror 502 at angled end 504. In these examples, mirror 502 is a mirrored surface formed on angled end 504. Mirror 502 is an example of mirror 304 in FIG. 3. Angled end 504 is opposite to end 506.

Prism 500 also has side 508, which is coupled to surface 510 of transparency 404. Side 508 may be coupled to transparency 404 using a coupling agent. A coupling agent is any composition that allows light to travel between prism 500 and transparency 404. This coupling agent is used to minimize the loss of light due to reflection or refraction. The coupling agent may be, for example, a glycol based fluid or glycerin. This coupling agent is an optical coupling agent that may be a gel or a fluid. In this example, light source 514 is present and transmits light through angled end 504 into prism 500 through surface 510. Light source 514 is an example of light source 306 in FIG. 3.

In this example, transparency 404 is attached to structural frame 406 through fastener system 518, which comprises bolt 520 and nut 522. Structure 516 is a cross-section of structural frame 406 taken along lines A-A in FIG. 4. Bolt 520 extends through hole 524 in transparency 404. Bolt 520 also extends through flange 526 in structural frame 406 and also through outside flange 528. Additionally, structural frame 406, flange 528, in combination with flange 526, makes inspection of hole 524 more difficult. The location of hole 524 within flange 526 in structural frame 406 and outside flange 528 makes a visual unaided inspection difficult or impossible. Further, the depth at which hole 524 is from end 530 of flange 526 and flange 528 makes the use of a simple prism difficult or impossible to use in inspecting the condition of hole 524.

The different advantageous embodiments recognize that a simple optical prism may be used, in many cases, in inspecting the attachment of a transparency to a structure. In some cases, however, the depth at which the attachment occurs is deep enough to make using conventional prisms impractical, because these types of prisms are unable to gather enough light to provide a viewer a good view of the hole where the fastener passes through the transparency. Further, in addition to lacking light, the currently available prisms are unable to provide an optical path due to the geometry. Thickness of the transparency is also a factor. The thinner the transparency the more difficult it is to view the fastener locations (due to a smaller optical window).

In this example, a viewer or operator may be present at view point 532, which has line of sight 534, which extends into side 538 of prism 500. Line of sight 534 is bent or redirected towards hole 524 along directed line of sight 536 by mirror 502 on angled end 504. The angle of mirror 502 is selected to redirect the light to the attachment point, hole 524.

Additionally, light source 514 transmits light though prim 500 and into transparency 404 in a direction that is around or substantially co-axial with directed line of sight 536. A response is received along directed line of sight 536, which is redirected back to line of sight 534 by mirror 502 on angled end 504 into view point 532 of the operator or other type of viewer.

In this manner, the optical inspection apparatus including prism 500, mirror 502, and light source 514 provides a viewer an ability to inspect the attachment of transparency 404 to structural frame 406. In particular, this apparatus allows a viewer to inspect hole 524 to determine whether cracks have occurred at this point of attachment.

This type of inspection may be performed at different stages. For example, the inspection may be performed after assembly of transparency 404 within structural frame 406. The inspection also may occur at a later point when an aircraft is in service during maintenance of the aircraft.

Further, although transparency 404 and structural frame 406 are shown in a configuration for a canopy of an aircraft, the different advantageous embodiments may be applied to other types of structures and transparencies attached to each other. For example, the optical inspection apparatus, in this example, may be used to inspect a window in a passenger aircraft. Further, the inspection may be made for other types of attachments, other than the use of a fastener, through a hole in the transparency. As an example, without limitation, the optical inspection apparatus, in the different advantageous embodiments, also may be used to examine a bonding of a transparency with a structure.

This apparatus also may be used to determine whether the material used to bond the transparency to the structure is intact or needs repair. Further, the apparatus of the different advantageous embodiments may be applied to transparencies and structures that are present in products other than aircraft. For example, the different advantageous embodiments may be applied to inspecting windows in a building, windows in a submarine, or windows or canopies in a spacecraft.

Figure 6:
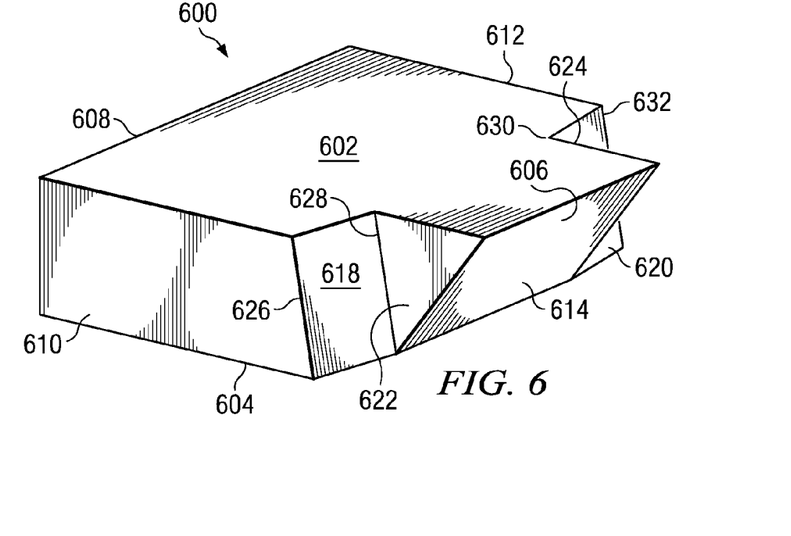
FIG. 6 is a perspective view of a prism in an optical inspection apparatus in accordance with an advantageous embodiment.

Turning now to FIG. 6, a perspective view of a prism in an optical inspection apparatus is depicted in accordance with an advantageous embodiment. In this example, prism 600 is an example of a prism, such as prism 500 in FIG. 5. Prism 600 includes side 602, side 604, angled end 606, end 608, side 610, and side 612. Side 602 and side 604 are opposite to each other and substantially around parallel to each other. Side 610 and side 612 are opposite to each other in prism 600 and are around or substantially parallel to each other. In other embodiments, sides 602 and 604 and sides 610 and 612 do not necessarily need to be parallel or substantially parallel to each other. Further, end 608 also may be an angled surface, depending on the particular implementation. Additionally, in these examples, the surface of sides 602, 604, and end 614 are polished flat and smooth for optical clarity. In prism 600, angled end 606 is opposite to end 608, in these examples.

Angled end 606 may include surface 614, on which a mirror may be attached or formed. As can be seen, surface 614 has a steeper angle than sections 618 and 620. As can be seen, in this example, section 618 is located between edges 626 and 628. Section 620 is located between edges 630 and 632, in these examples. In this view, angled end 606 includes triangular sides 622 and 624. Triangular sides 622 and 624 may be opaque. These ends may be made opaque by painting them black, in these examples. Further, end 608 also may be made opaque by painting this end black, in these examples. Painting the unused portions of prism 600 black prevents unwanted reflections within prism 600. Multiple reflections can obscure the intended image. Although black is the color used in these examples, other colors may be used that prevent reflections within prism 600.

In these examples prism 600 may be made of various materials. For example, prism 600 may be made of acrylic or acrylic glass. Acrylic glass may be polymethyl methacrylate. When using acrylic, the acrylic may be a cast acrylic or a stretched acrylic. Examples of other materials that may be used for prism 600 include, for example, without limitation, polycarbonate, fused quartz, and fused silica. Of course, any transparent material may be used.

In these examples, the material used for prism 600 may be selected to have a refractive index that matches or is close to the refractive index of the material that is being inspected. By selecting refractive indexes that are close to each other, the angles for inspection may be made easier. Optical materials with a higher index of refraction bend light more and optical materials with a lower index of refraction bend light less. In these examples, the index of the prism is matched with the index of the transparency. This matching makes the geometry of the optics simple. Of course, in some embodiments, the index of refraction does not need to be matched. For example, in one example, a complex geometry or difficult to access transparency may use an optical inspection apparatus with a prism that is made of a different material, having a different index refraction, to change the optical line of sight to provide for inspection of the item of interest.

Figure 7:
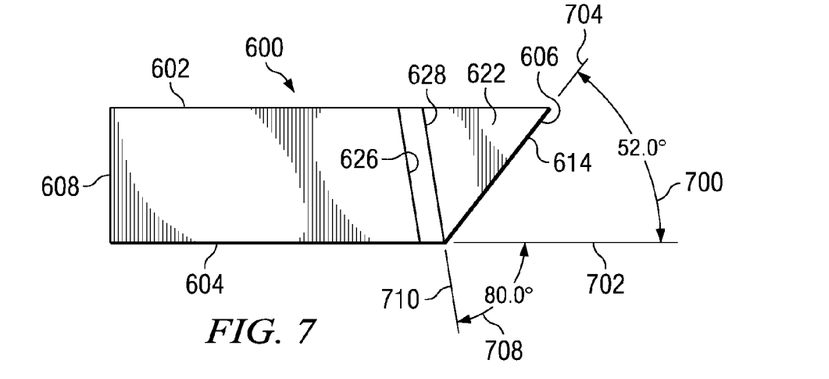
FIG. 7 is a side view of the prism in accordance with an advantageous embodiment.

Turning now to FIG. 7, a side view of prism 600 is illustrated. In this example, angled end 606 has angle 700, which is around 52.0 degrees, in this example.

Angle 700 is measured between plane 702 and plane 704. These planes are imaginary planes used to describe angles for the different features of prism 600. Plane 702 is plane on which surface 604 lies, and plane 704 is a plane on which surface 614 of angled end 606 lies. Prism 600 also includes angle 708, which is an angle between plane 702 and line 710, which follows edge 628 of prism 600.

Figure 8:
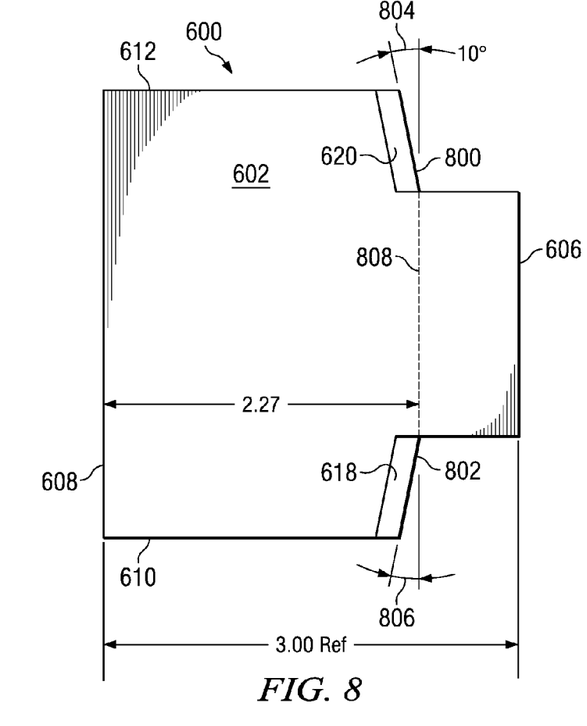
FIG. 8 is a top view of the prism in accordance with an advantageous embodiment.

Turning now to FIG. 8, a top view of prism 600 is depicted in accordance with an advantageous embodiment. In this example, prism 600 illustrates an angle for sections 618 and 620. In this example, edge 800 and edge 802 each have angles 804 and 806 respectively, which are both around 10 degrees, in this example. In these examples, prism 600 has a length of around 3.00 inches between end 608 and the upper edge of angled end 606. Prism 600 has a length of around 2.27 inches from end 608 to line 808.

Figure 9:
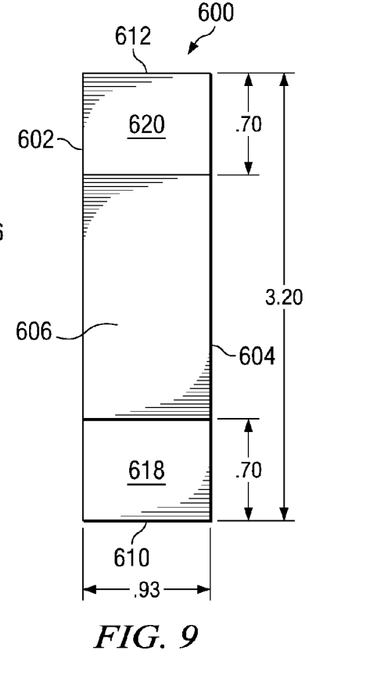
FIG. 9 is a view of the prism from an angled edge in accordance with an advantageous embodiment.

With reference now to FIG. 9, a side view of prism 600 from angled end 606 is depicted in accordance with an advantageous embodiment. As can be seen in this example, the distance between side 602 and side 604 is around 0.93 inches. The width of sections 618 and 620 is around 0.70 inches. The width from side 610 to side 612 is around 3.20 inches.

The different values for the angles and dimensions of prism 600 are presented for purposes of illustrating one advantageous embodiment. Other advantageous embodiments may have other angles, values for dimensions and optical materials with various indices of refraction. The particular angles and dimensions selected may vary, depending on the implementation. In some advantageous embodiments, the different dimensions and angles are selected to provide a line of sight and a directed line of sight to allow an inspection of a transparency or transparent material attached to a structure, in which the attachment mechanism may be difficult to see because of the location of the attachment mechanism within the structure.

Figure 10:
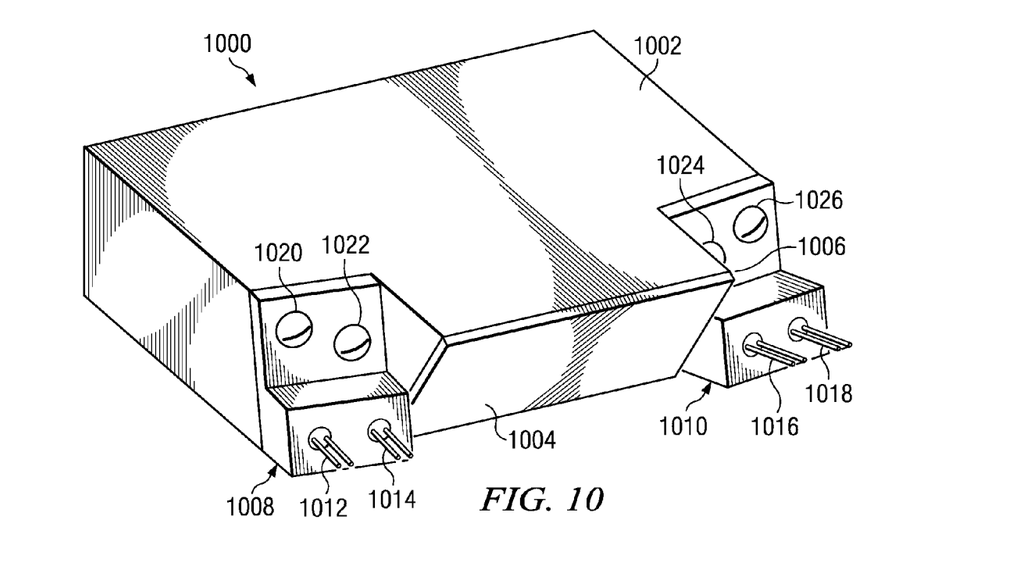
FIG. 10 is a diagram illustrating an optical inspection apparatus in accordance with an advantageous embodiment.

Turning now to FIG. 10, a diagram illustrating an optical inspection apparatus is depicted in accordance with an advantageous embodiment. In this example, optical inspection apparatus 1000 is an example of optical inspection apparatus 300 in FIG. 3. Prism 1002 is an example of prism 302 in FIG. 3 and may be implemented using a prism having a configuration of prism 600 as illustrated in FIGS. 6-9. In this example, mirror 1004 is attached to angled end 1006. In these examples, mirror 1004 may be a mirror that is bonded to angled end 1006 with an optical adhesive. In other examples, mirror 1004 may be a mirror formed on the surface of angled end 1006.

Additionally, optical inspection apparatus 1000 includes a set of light emitting diodes, which may be one or more diodes. In the depicted examples, the set of light emitting diodes are located in light emitting diode units 1008 and 1010. These light emitting diode units are examples of light source 306 in FIG. 3. In these examples, each light emitting diode unit has two light emitting diodes. Leads 1012, 1014, 1016, and 1018 are leads for the light emitting diodes within light emitting diode units 1008 and 1010. These light emitting diode units are attached to prism 1002 such that these units transmit or project light at an angle that is around or substantially coaxial along a reflective line of sight, such as reflective line of sight 536 in FIG. 5. In these examples, light emitting diode units 1008 and 1010 are attached to prism 1002 through fasteners 1020, 1022, 1024, and 1026.

Figure 11:
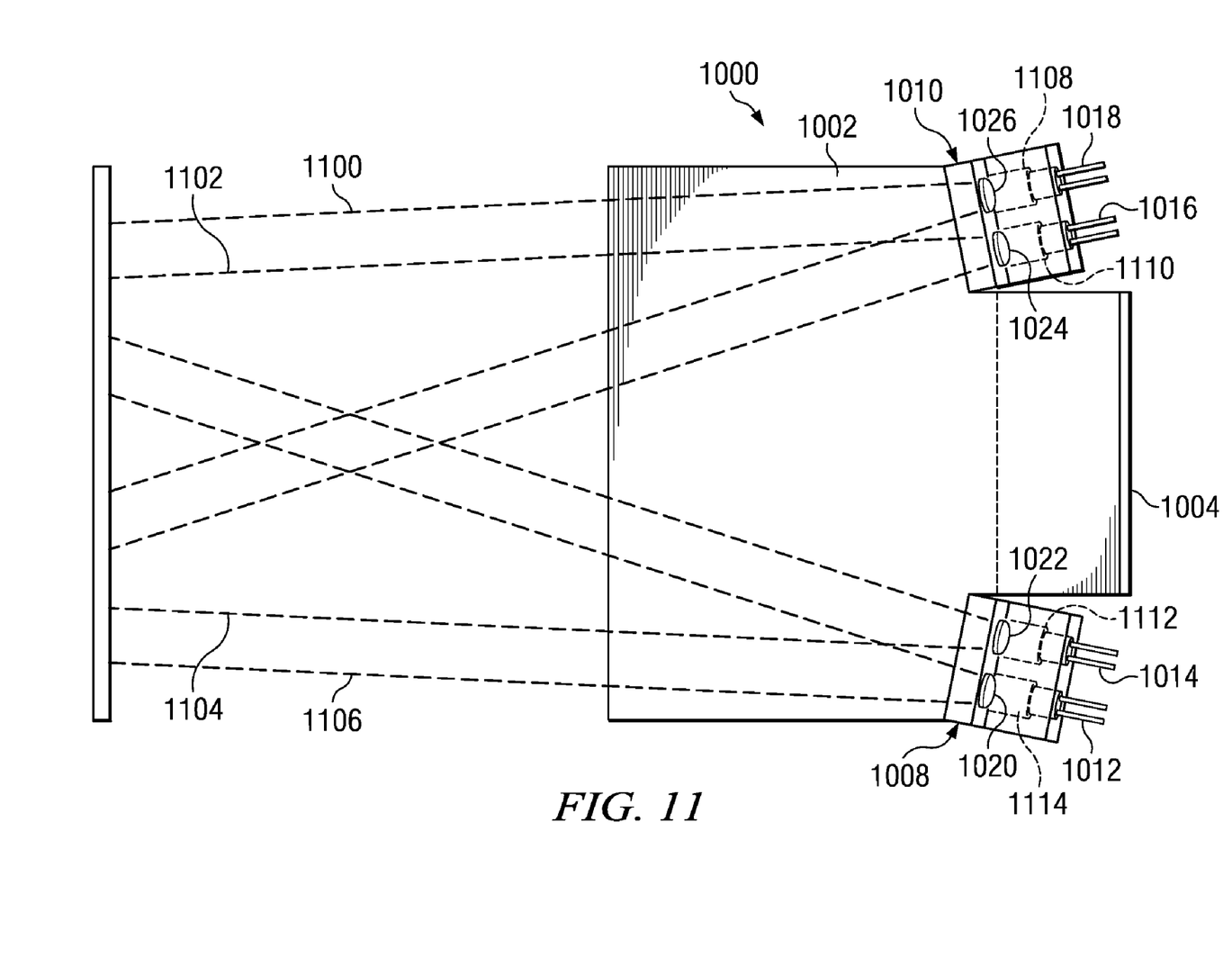
FIG. 11 is a diagram illustrating a top view of an optical inspection apparatus in accordance with an advantageous embodiment.

Turning now to FIG. 11, a diagram illustrating a top view of an optical inspection apparatus is depicted in accordance with an advantageous embodiment. In this example, optical inspection apparatus 1000 illustrates the transmission of light through prism 1002 by light emitting diode units 1008 and 1010. In these examples, light projections 1100, 1102, 1104, and 1106 are generated by light emitting diodes 1108, 1110, 1112, and 1114 in light emitting diode units 1008 and 1010 and illustrate the light transmitted by each of the light emitting diodes.

Figure 12:
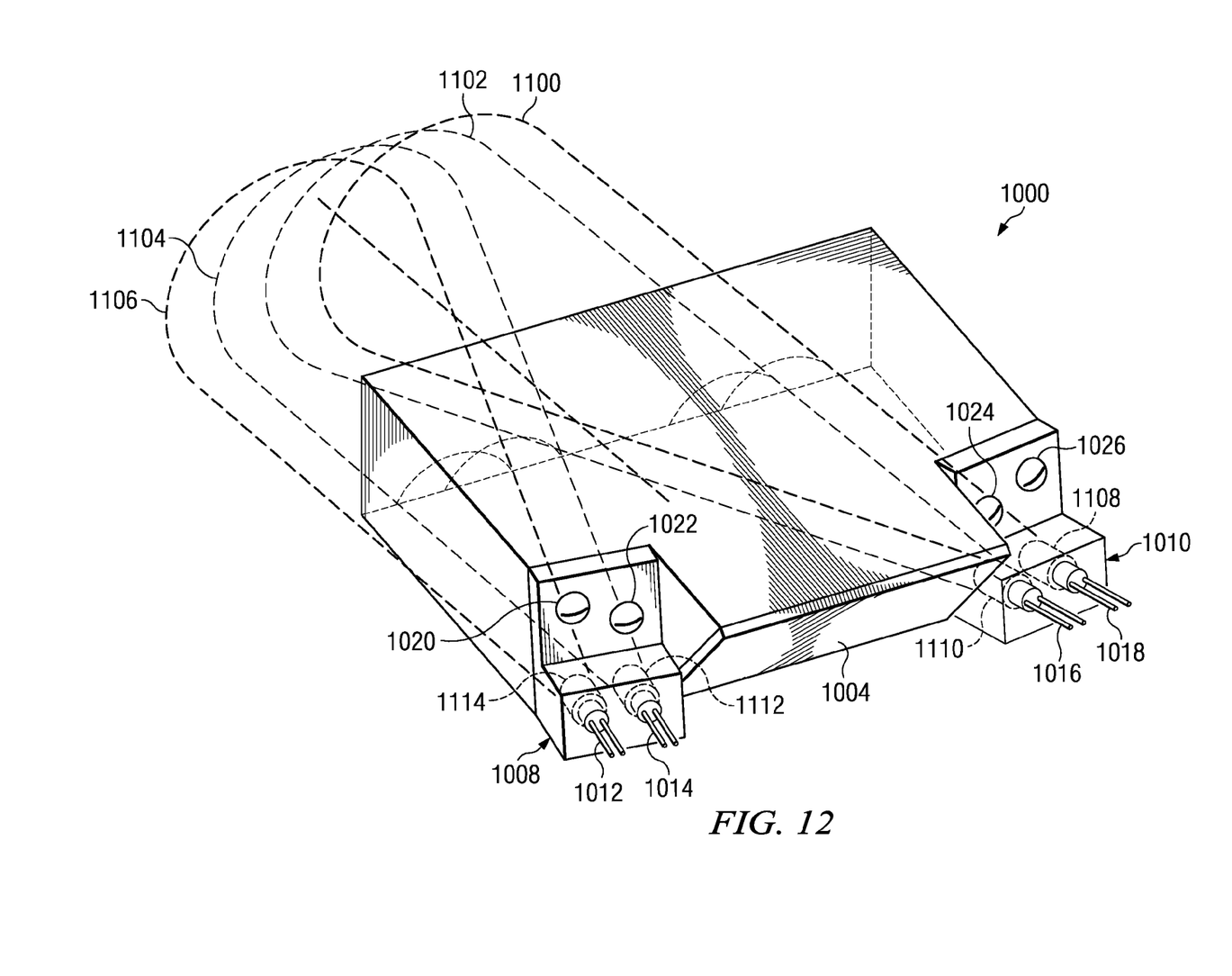
FIG. 12 is a diagram illustrating a perspective view of an optical inspection apparatus in accordance with an advantageous embodiment.

With reference now to FIG. 12, a perspective view of optical inspection apparatus 1000 provides another view of light projections 1100, 1102, 1104, and 1106.

Figure 13:
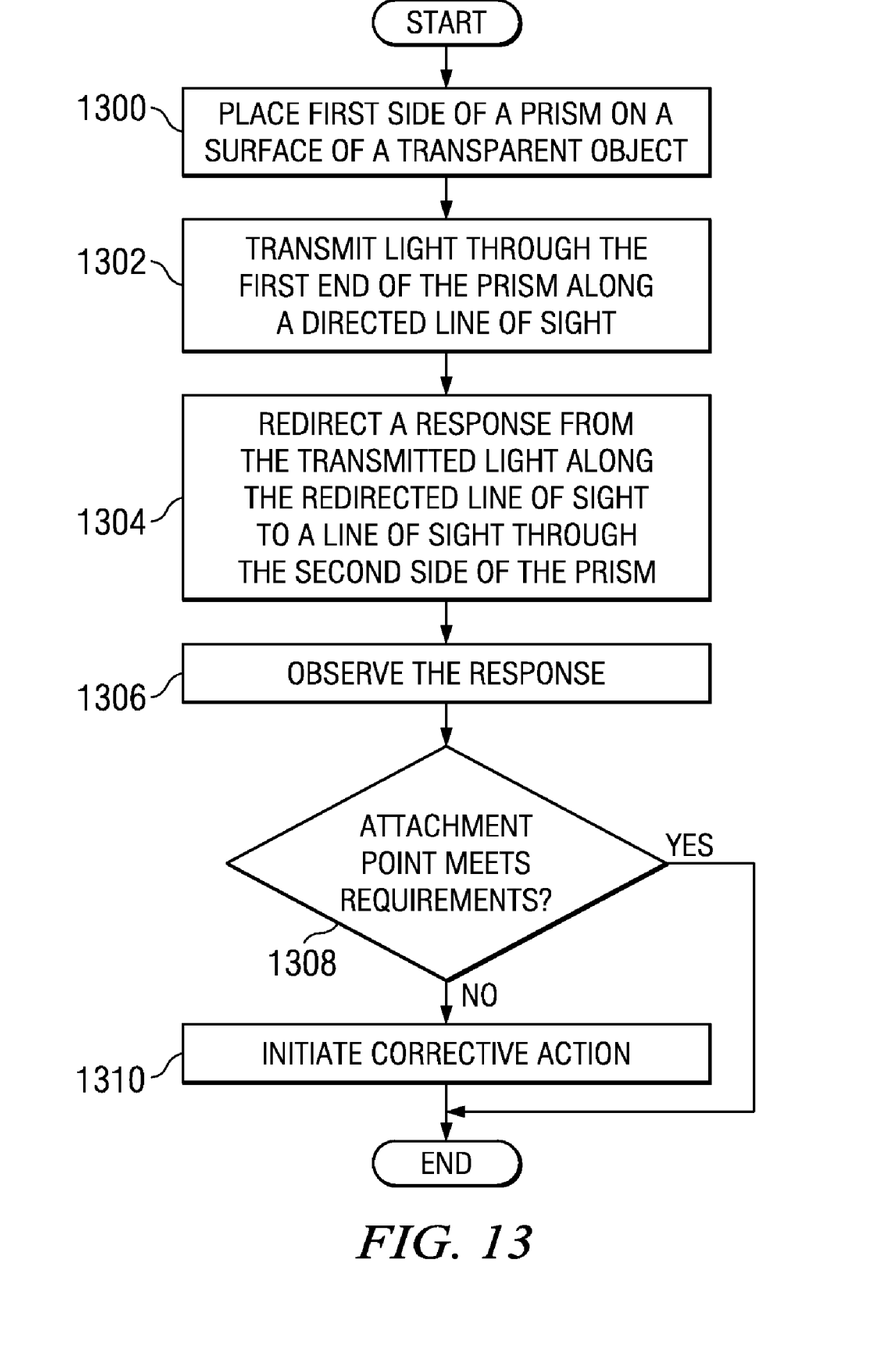
FIG. 13 is a flowchart of a process for inspecting a transparent object attached to a structure in accordance with an advantageous embodiment.

With reference now to FIG. 13, a flowchart of a process for inspecting a transparent object attached to a structure is depicted in accordance with an advantageous embodiment. The process illustrated in FIG. 13 may be implemented using an optical inspection apparatus, such as optical inspection apparatus 300 in FIG. 3. In these examples, the optical inspection apparatus may be used to inspect attachment points between a transparent object and a structure. In these examples, the transparent object is a transparency for a canopy that is attached to a structural frame. The attachment points are holes through which fasteners are placed to attach the transparency to the structural frame. In other embodiments, the attachment may consist of a surface in which a bonding agent has been placed to attach a transparent object to a structure. The process illustrated in FIG. 13 may be implemented to inspect attachment points or surfaces that are usually not visible to a viewer without aid. Further, these different advantageous embodiments allow for redirecting the line of sight in a manner that is unavailable with a prism.

The process begins by placing a first side of a prism on a surface of a transparent object (operation 1300). This operation also includes coupling the prism to the surface with a coupling agent. This surface is opposite to the line of sight of a viewer, in these examples.

Next, the process transmits light through the first end of the prism along a directed line of sight (operation 1302). In these examples, the light is generated by a light source that is integrated or attached to the prism.

A response received from the transmitted light is redirected to the line of sight from the directed line of sight through the second side of the prism (operation 1304). This line of sight terminates or passes through an observation point for the viewer. In this manner, the viewer may look into the second side of the prism on the surface of the transparent object and view an attachment point that is along a different line of sight. In this case, this redirected line of sight may be 90 or around 90 degrees to the direction of the attachment point along the transparent object. Of course, the angle may vary, depending on the particular implementation and the desired viewing point. This angle may be varied by altering the angle of the mirror on the first end of the prism.

In these examples, the light is redirected from the directed line of sight using a mirror that is located on an angled portion of the first end.

The response is then observed at the observation point (operation 1306). A determination is made as to whether the attachment point meets the requirements (operation 1308). These requirements may vary, depending on the particular implementation. For example, one requirement may be that an absence of any crack or wear is present at the hole at which the fastener attaches the transparency to the frame of the canopy. In another embodiment, the requirement may be that the bonding agent or material appears to be intact at the point of attachment. The actual requirements used may depend on the particular implementation. If the attachment point does not meet the requirement, a corrective action is initiated (operation 1310), with the process terminating thereafter. This corrective action may be, for example, to replace the transparent object with another transparent object. In other cases, if a bonding agent is used, the transparent object may be removed from the structure. The old bonding agent may be removed and a new bonding agent may be reapplied with the transparent object then being placed back into the structure. If the inspection meets the requirements in step 1308, then no action is taken and the process terminates. This process may be repeated for different attachment points between the transparent object and the structure, or for other transparent objects in structure assemblies.

The description of the different advantageous embodiments has been presented for purposes of illustration and description, and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An optical inspection apparatus comprising:
   a prism having a first end, a first side, and a second side, wherein the first side is opposite the second side, the first side is around parallel to the second side, the first end is located between the first side and the second side, the first end has an angled surface, and the prism is capable of bending light;
   a mirror located on the angled surface, wherein the minor is capable of redirecting light entering the prism on the first side along a directed line of sight to the second side opposite to the first side along a line of sight to a viewer; and
   a light source attached to another surface on the first end of the prism, wherein the light source is capable of transmitting light through the prism along an axis that is approximately coaxial to the directed line of sight.

2. The optical inspection apparatus of claim 1, wherein the angled surface has an angle of around 52 degrees with respect to a plane on which the first side lies.

3. The optical inspection apparatus of claim 1, wherein the minor is selected from one of a mirrored surface formed on the angled surface and an optical minor attached to the angled surface.

4. The optical inspection apparatus of claim 1, wherein the prism is formed from a material selected from one of polymethyl methacrylate and polycarbonate.

5. The optical inspection apparatus of claim 1, wherein the light source is a set of light emitting diodes.

6. The optical inspection apparatus of claim 1, wherein the prism has a second end opposite to the first end in which the second end is opaque.

7. An apparatus comprising:
   an optical prism having a first side, a second side and a first end, wherein the first side is opposite the second side;
   a minor located on the first end, wherein the mirror is capable of reflecting light from a directed line of sight through the second side to a selected point to a line of sight through the first side; and
   a light source attached to the first end on which the angled surface is located, wherein the light source is capable of transmitting light along an axis that is approximately coaxially aligned to the directed line of sight.

8. The apparatus of claim 7, wherein the minor is located on an angled surface at a first end of the optical prism.

9. The apparatus of claim 8, wherein the mirror is selected from one of a mirrored surface formed on the angled surface and an optical minor attached to the angled surface.

10. The apparatus of claim 7, wherein the light source comprises a first light emitting diode unit and a second light emitting diode unit, wherein the first light emitting diode units and the second light emitting diode units are attached to the first end.

11. The apparatus of claim 7, wherein the optical prism is formed from a material selected from one of polymethyl methacrylate and polycarbonate.

12. A method for inspecting a transparent object attached to a structure, the method comprising:

placing a first side of a prism onto a surface of the transparent object attached to the structure, wherein an attachment point is present between the transparent object and the structure below a surface of the structure;

transmitting a light through a first side of the prism along a directed line of sight to the attachment point of the transparent object;

redirecting a response to the transmitted light from the directed line of sight to a line of sight through a second side of the prism that is opposite to the first side with a mirror; wherein the first end of the prism is located between the first side and the second side of the prism, wherein the first end has an angled surface, wherein the mirror for the prism is located on the angled surface, and wherein the prism has a light source attached to another surface on the first end of the prism and transmits the light source;

observing the response to view the attachment point; and determining whether the attachment point meets a requirement.

13. The method of claim 12 further comprising:

initiating a corrective action in response to a determination that the attachment point does not meet the requirement.

14. The method of claim 12, wherein the attachment point comprises a hole in the transparent object.

15. The method of claim 14, wherein the requirement is an absence of a crack in the transparent object around the attachment point.

16. The method of claim 12, wherein the attachment point comprises a bonding agent.

17. The method of claim 12, wherein the transparent object is a transparency for a canopy and the structure is a frame for the canopy.

18. The method of claim 12, wherein the transparent object is a window in a frame for a submarine, a spacecraft, an aircraft, a ship, or a building.

* * * * *